US010136902B2

(12) United States Patent
Farris

(10) Patent No.: US 10,136,902 B2
(45) Date of Patent: Nov. 27, 2018

(54) SURGICAL INSTRUMENT AND METHOD

(71) Applicant: Warsaw Orthopedic, Inc., Warsaw, IN (US)

(72) Inventor: Robert A Farris, Cordova, TN (US)

(73) Assignee: Warsaw Orthopedic, Inc., Warsaw, IN (US)

(*) Notice: Subject to any disclaimer, the term of this patent is extended or adjusted under 35 U.S.C. 154(b) by 470 days.

(21) Appl. No.: 14/814,801

(22) Filed: Jul. 31, 2015

(65) Prior Publication Data
US 2017/0027592 A1 Feb. 2, 2017

(51) Int. Cl.
*A61B 17/16* (2006.01)
*A61B 90/00* (2016.01)

(52) U.S. Cl.
CPC ...... *A61B 17/1671* (2013.01); *A61B 17/1615* (2013.01); *A61B 17/1628* (2013.01); *A61B 17/1655* (2013.01); *A61B 2090/062* (2016.02)

(58) Field of Classification Search
CPC . A61B 17/16; A61B 17/1615; A61B 17/1617; A61B 17/1628; A61B 17/1655; A61B 17/1662; A61B 17/1671
USPC .......................................... 606/80, 315–318
See application file for complete search history.

(56) References Cited

U.S. PATENT DOCUMENTS

| 3,892,232 | A | * | 7/1975 | Neufeld | A61B 17/742 606/104 |
| 5,593,410 | A | * | 1/1997 | Vrespa | A61B 17/863 606/312 |
| 6,068,632 | A | * | 5/2000 | Carchidi | A61B 17/1635 433/165 |
| 8,523,873 | B2 | * | 9/2013 | Bharadwaj | A61B 17/1633 600/554 |
| 8,814,914 | B2 | * | 8/2014 | Miller | A61B 17/1671 606/279 |
| 9,615,894 | B2 | * | 4/2017 | Jorneus | A61B 17/1655 |
| 2003/0018337 | A1 | * | 1/2003 | Davis | A61B 17/1655 606/80 |
| 2004/0092940 | A1 | * | 5/2004 | Zwirnmann | A61B 17/1633 606/80 |
| 2004/0260291 | A1 | * | 12/2004 | Jensen | A61B 17/1655 606/915 |
| 2005/0038438 | A1 | * | 2/2005 | Anderson | A61B 17/7071 606/304 |
| 2005/0070907 | A1 | * | 3/2005 | Abernathie | A61B 17/1655 606/80 |
| 2005/0107800 | A1 | * | 5/2005 | Frankel | A61B 17/1655 606/92 |
| 2007/0055249 | A1 | * | 3/2007 | Jensen | A61B 17/1655 606/288 |
| 2007/0099153 | A1 | * | 5/2007 | Fromovich | A61C 8/0022 433/174 |
| 2007/0162018 | A1 | * | 7/2007 | Jensen | A61B 17/1655 606/326 |
| 2007/0293867 | A1 | * | 12/2007 | Anitua | A61B 17/1615 606/80 |
| 2008/0051793 | A1 | * | 2/2008 | Erickson | A61B 17/1655 606/279 |

(Continued)

*Primary Examiner* — Eric S Gibson

(57) ABSTRACT

A surgical instrument comprises a proximal end including a tool engagement surface. A distal end is configured to form a bore in vertebral tissue. The distal end includes a first thread, a second thread spaced from the first thread and at least one tissue depth indicia. Systems and methods are disclosed.

18 Claims, 7 Drawing Sheets

(56) References Cited

U.S. PATENT DOCUMENTS

| | | | |
|---|---|---|---|
| 2009/0210016 A1* | 8/2009 | Champagne | A61B 17/863 606/309 |
| 2010/0009314 A1* | 1/2010 | Tardieu | A61C 1/084 433/144 |
| 2010/0030218 A1* | 2/2010 | Prevost | A61B 17/1655 606/80 |
| 2010/0324562 A1* | 12/2010 | Thomsen | A61B 17/1604 606/80 |
| 2011/0054537 A1* | 3/2011 | Miller | A61B 17/1655 606/279 |
| 2011/0251597 A1* | 10/2011 | Bharadwaj | A61B 17/1633 606/1 |
| 2012/0191097 A1* | 7/2012 | Jorneus | A61C 8/0089 606/80 |
| 2012/0191103 A1* | 7/2012 | Jorneus | A61B 17/1655 606/96 |
| 2012/0245585 A1* | 9/2012 | Kaiser | A61B 17/1633 606/80 |
| 2013/0211468 A1* | 8/2013 | Huebner | A61B 17/863 606/328 |
| 2014/0100575 A1* | 4/2014 | Yim | A61B 17/1655 606/80 |
| 2015/0245845 A1* | 9/2015 | Grinberg | A61B 17/16 606/80 |
| 2016/0135920 A1* | 5/2016 | Jorneus | A61B 17/1655 433/174 |
| 2017/0027592 A1* | 2/2017 | Farris | A61B 17/1671 |

\* cited by examiner

SURGICAL INSTRUMENT AND METHOD

TECHNICAL FIELD

The present disclosure generally relates to medical devices for the treatment of musculoskeletal disorders, and more particularly to a surgical system for preparing a surgical site, and a method for treating a spine.

BACKGROUND

Spinal pathologies and disorders such as scoliosis and other curvature abnormalities, kyphosis, degenerative disc disease, disc herniation, osteoporosis, spondylolisthesis, stenosis, tumor, and fracture may result from factors including trauma, disease and degenerative conditions caused by injury and aging. Spinal disorders typically result in symptoms including deformity, pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes fusion, fixation, corpectomy, discectomy, laminectomy and implantable prosthetics. For example, fusion and fixation treatments may be performed that employ implants to restore the mechanical support function of vertebrae. Surgical instruments are employed, for example, to prepare tissue surfaces for disposal of the implants. Surgical instruments are also employed to engage implants for disposal with the tissue surfaces at a surgical site. This disclosure describes an improvement over these prior technologies.

SUMMARY

In one embodiment, a surgical instrument is provided. The surgical instrument comprises a proximal end including a tool engagement surface. A distal end is configured to form a threaded bore in vertebral tissue. The distal end includes a first thread, a second thread spaced from the first thread and at least one tissue depth indicia. In some embodiments, surgical systems and methods are provided.

BRIEF DESCRIPTION OF THE DRAWINGS

The present disclosure will become more readily apparent from the specific description accompanied by the following drawings, in which.

DETAILED DESCRIPTION

Figure 1:
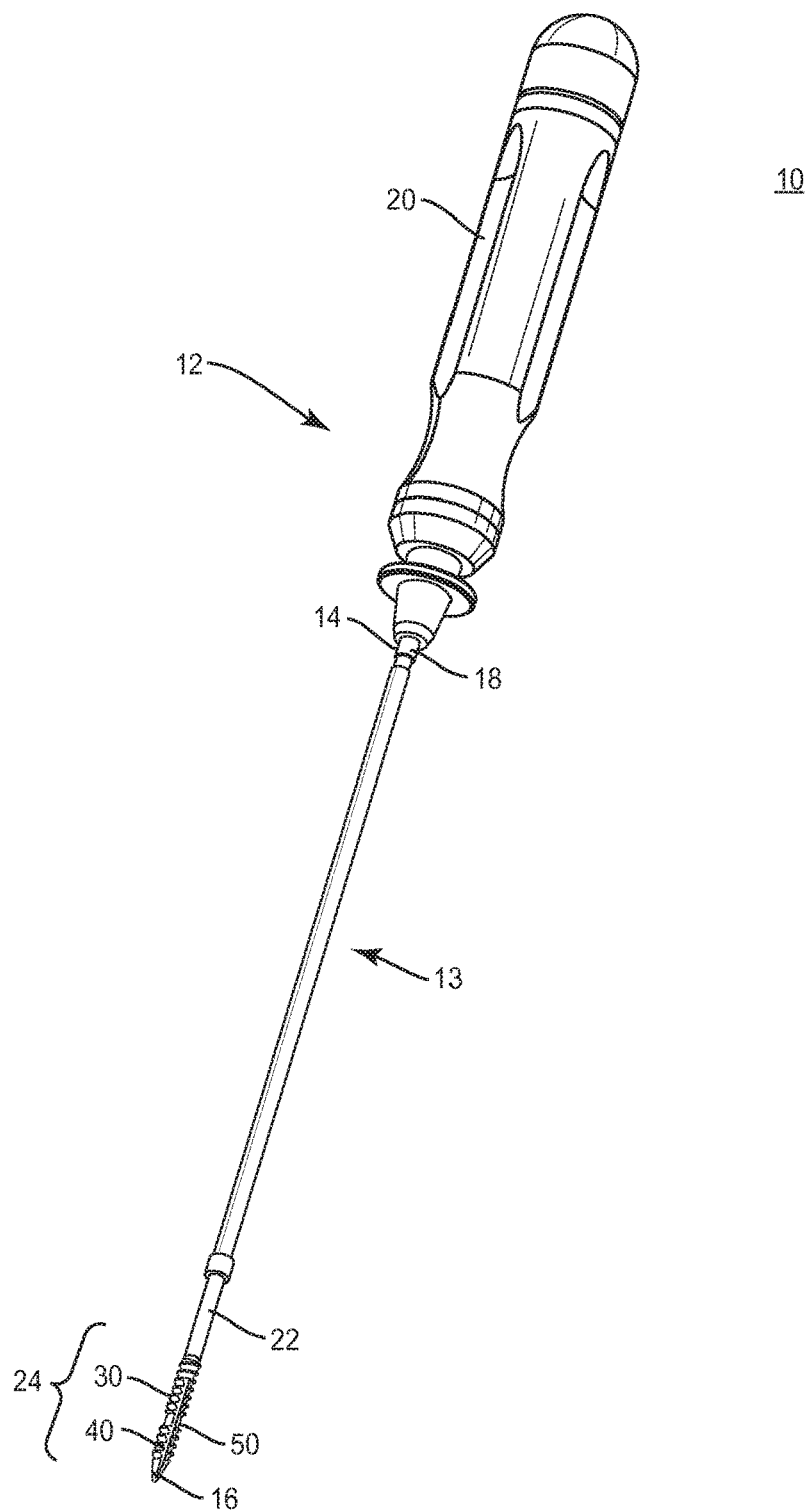
FIG. 1 is a perspective view of components of one embodiment of a surgical system in accordance with the principles of the present disclosure.

The exemplary embodiments of a surgical system are discussed in terms of medical devices for the treatment of musculoskeletal disorders and more particularly, in terms of a surgical system for preparing a surgical site, and a method for treating a spine.

In some embodiments, the surgical system includes a surgical instrument, such as, for example, a bone tap. In some embodiments, the bone tap is utilized to prepare tissue, such as, for example, bone to receive a fastener, such as, for example, a bone screw. In some embodiments, the surgical system is employed with a method such that a surgeon only partially taps the bone to facilitate starting the bone screw in tissue. In some embodiments, the method can include tapping a cervical lateral mass for treatment of a spine and fixation of vertebrae. In some embodiments, the method includes the step of tapping bone to a partial depth of 10 millimeters (mm). In some embodiments, the method includes the step of tapping bone for implanting a bone screw having a length of 14 mm.

In some embodiments, the surgical system includes a bone tap having at least one tissue depth indicia, such as, for example, an undercut on tap threads that are configured to provide a visual depth indicator. In some embodiments, the surgical system includes a 10 mm visual depth indicator. In some embodiments, the surgical system includes a 14 mm visual depth indicator. In some embodiments, the surgical system is employed with a method to provide a visual reference for determining a depth of the bone tap in tissue, such as, for example, a lateral mass for partial or full tapping of tissue. In some embodiments, the surgical instrument can be utilized with other procedures and using various depths and one or a plurality of undercuts.

In some embodiments, one or all of the components of the surgical system may be disposable, peel pack and/or pre packed sterile devices. One or all of the components of the surgical system may be reusable. The surgical system may be configured as a kit with multiple sized and configured components.

In some embodiments, the surgical system of the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. In some embodiments, the surgical system of the present disclosure may be employed with other osteal and bone related applications, including those associated with diagnostics and therapeutics. In some embodiments, the surgical system may be alternatively employed in a surgical treatment with a patient in a prone or supine position, and/or employ various surgical approaches to the spine, including anterior, posterior, posterior mid-line, lateral, postero-lateral, and/or antero-lateral approaches, and in other body regions. The surgical system of the present disclosure may also be alternatively employed with procedures for treating the lumbar, cervical, thoracic, sacral and pelvic regions of a spinal column. The surgical system of the present disclosure may also be used on animals, bone models and other non-living substrates, such as, for example, in training, testing and demonstration.

The surgical system of the present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. In some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

As used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, microdiscectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. As used in the specification and including the appended claims, the term "tissue" includes soft tissue, ligaments, tendons, cartilage and/or bone unless specifically referred to otherwise.

Figure 2:
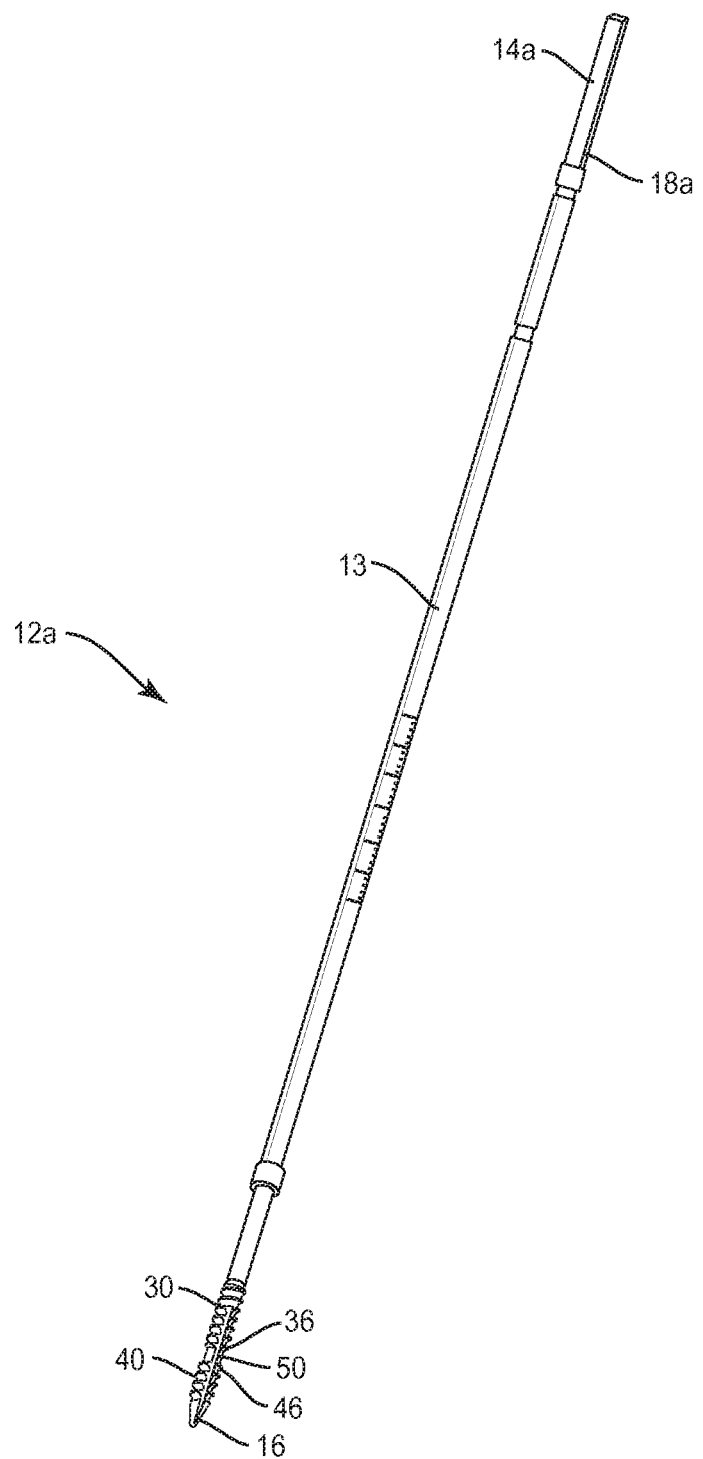
FIG. 2 is a perspective view of components of one embodiment of a surgical system in accordance with the principles of the present disclosure.
Figure 3:
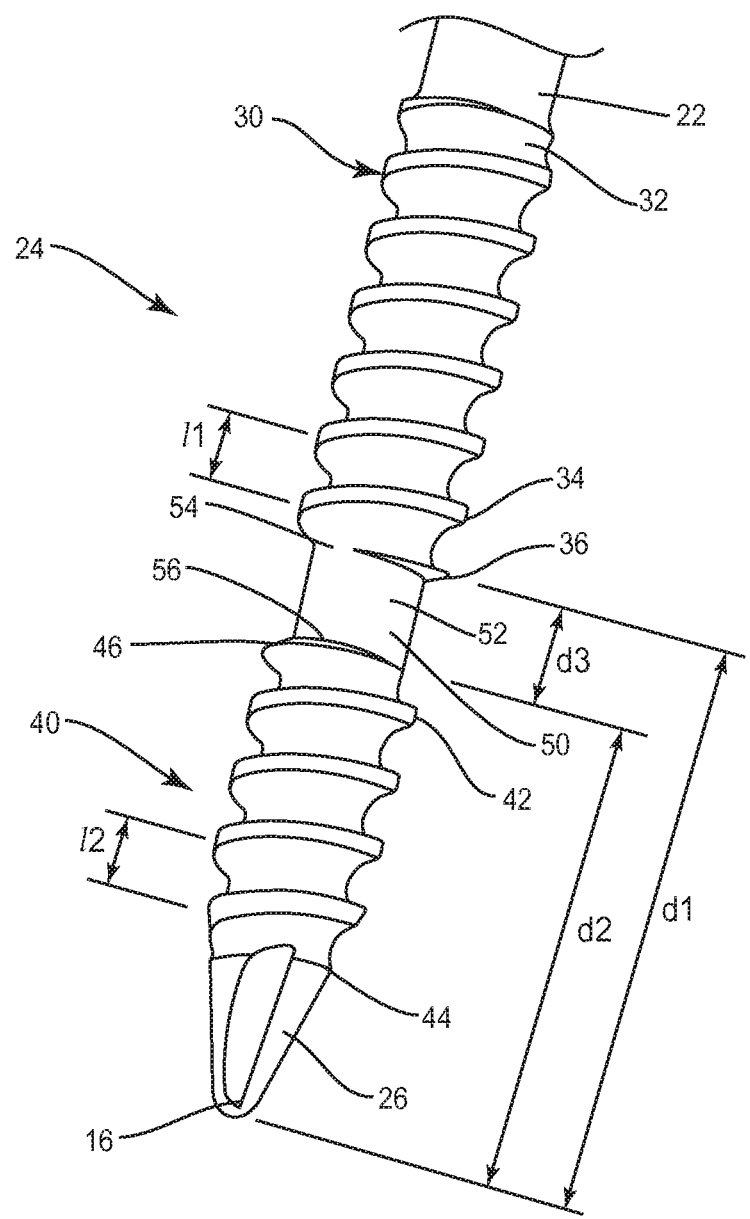
FIG. 3 is a break away view of components of the system shown in FIG. 1.

The following discussion includes a description of a surgical system including a surgical instrument, related components and methods of employing the surgical system in accordance with the principles of the present disclosure. Alternate embodiments are also disclosed. Reference is made in detail to the exemplary embodiments of the present disclosure, which are illustrated in the accompanying figures. Turning to FIGS. 1-3, there are illustrated components of a surgical system 10.

The components of surgical system 10 can be fabricated from biologically acceptable materials suitable for medical applications, including metals, synthetic polymers, ceramics and bone material and/or their composites. For example, the components of surgical system 10, individually or collectively, can be fabricated from materials such as stainless steel alloys, aluminum, commercially pure titanium, titanium alloys, Grade 5 titanium, super-elastic titanium alloys, cobalt-chrome alloys, superelastic metallic alloys (e.g., Nitinol, super elasto-plastic metals, such as GUM METAL®), ceramics and composites thereof such as calcium phosphate (e.g., SKELITE™), thermoplastics such as polyaryletherketone (PAEK) including polyetheretherketone (PEEK), polyetherketoneketone (PEKK) and polyetherketone (PEK), carbon-PEEK composites, PEEK-$BaSO_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations.

Various components of surgical system 10 may have material composites, including the above materials, to achieve various desired characteristics such as strength, rigidity, elasticity, compliance, biomechanical performance, durability and radiolucency or imaging preference. The components of surgical system 10, individually or collectively, may also be fabricated from a heterogeneous material such as a combination of two or more of the above-described materials. The components of surgical system 10 may be monolithically formed, integrally connected or include fastening elements and/or instruments, as described herein.

Surgical system 10 is employed, for example, with an open or mini-open, minimal access and/or minimally invasive including percutaneous surgical technique to create a cavity for an implant, such as, for example, a bone fastener at a surgical site within a body of a patient, for example, a section of a spine. In one embodiment, the components of surgical system 10 are configured to create a cavity in vertebrae to fix a spinal rod, connector and/or plate to a spine via a bone fastener for a surgical treatment to treat various spine pathologies, such as those described herein.

Surgical system 10 comprises a surgical instrument, such as, for example, a tissue tap 12. Tap 12 includes a shaft 13 that extends between an end, such as, for example, a proximal end 14 and an end, such as, for example, a distal end 16. End 14 includes a tool engagement surface 18. In some embodiments, surface 18 is configured for engagement and connection with a handle 20, as shown in FIG. 1. Handle 20 is configured to facilitate manipulation of tap 12. In some embodiments, handle 20 may have alternate cross section configurations, such as, for example, oval, oblong, triangular, square, hexagonal, polygonal, irregular, uniform, non-uniform and/or tapered. In some embodiments, handle 20 may be disposed at alternate orientations relative to end 14, such as, for example, transverse, perpendicular and/or other angular orientations such as acute or obtuse.

In some embodiments, end 14 and/or surface 18 are configured to engage an actuator, such as, for example, a surgical instrument, hand drill and/or driver to rotate end 16 in a first direction and/or an opposing second direction, such as, for example, clockwise and counter-clockwise directions. In some embodiments, end 14 and/or surface 18 may include a hexagonal cross sectional configuration and is configured to engage a correspondingly shaped portion of the actuator. In some embodiments, end 14 and/or surface 18 may include a square, triangular, polygonal, star or hexalobe cross sectional configuration configured to engage a correspondingly shaped portion of the actuator. In some embodiments, end 14 and/or surface 18 may include an interchangeable driving handle removably connected to end 14 such that torque applied manually or by a motorized actuator to handle 20 is transmitted to shaft 13.

In some embodiments, a tissue tap 12*a*, similar to tap 12, includes an end 14*a* and an engagement surface 18*a*. In some embodiments, end 14*a* and/or surface 18*a*, as shown in FIG. 2, are configured to engage an actuator, such as, for example, a motorized actuator, such as, for example, a powered drill (not shown). In some embodiments, the motorized actuator includes a mating connector, such as, for example, a chuck. In some embodiments, the chuck includes a socket that is configured to mate with end 14*a* and/or surface 18*a*. In some embodiments, the motorized actuator includes an electric motor, such as, for example, an electric drill motor that is connected to a power source, such as, for example, a battery and/or AC source, for rotating end 16. In one embodiment, the motorized actuator may be pneumatic or hydraulic.

End 16 is configured to form a bore in vertebral tissue, as described herein. End 16 includes a cylindrical shaft 22 including an external or male threaded portion 24 configured to form an internal or female thread in tissue such that an implant, such as, for example, a bone fastener, can be threaded into the internal thread formed by tap 12. In one embodiment, end 16 includes a tapered portion, such as for example, a tip 26 configured to facilitate self-tapping insertion of tap 12 into tissue. In some embodiments, tip 26 is blunt. In some embodiments, all or a portion of shaft 22 may have alternate cross section configurations, such as, for example, oval, oblong, triangular, square, hexagonal, polygonal, irregular, uniform, non-uniform and/or tapered.

Threaded portion 24 includes a proximal thread 30. Thread 30 extends between a proximal most end 32 and a distal most end 34. Thread 30 extends a distance along shaft 22 and includes a lead I1. In some embodiments, lead I1 includes an axial advance of a helix of thread 30 during one complete 360 degree rotation of thread 30. In some embodiments, end 34 is disposed at a position located 14 mm from a distal most end of tip 26. In some embodiments, end 34 is disposed at a position located 14 mm from a distal most end of a thread 40 described herein, which does not include tip 26. Thread 30 extends proximally from end 34 along shaft 22 to end 32 to facilitate tapping a desired depth for a bone fastener.

Thread 30 includes tissue depth indicia, such as, for example, an undercut 36 disposed adjacent end 34. Undercut 36 provides visual indicia of a depth of penetration of tissue, such as for example, a depth d1, relative to vertebrae. In some embodiments, undercut 36 comprises a stopping point of thread 30 and/or tap 12 relative to vertebrae. In some embodiments depth d1 is substantially equal to 14 mm. In some embodiments, all or a portion of thread 30, for example, undercut 36 may be radiopaque. In some embodiments, thread 30 includes a plurality of undercuts 36, which may be spaced apart.

In some embodiments, undercut 36 is configured to generate a tactile feedback and indicate a stage of insertion and/or penetration of tap 12 along thread 30. In one embodiment, undercut 36 provides a tactile feel to a surgeon when tap 12 is inserted to a partial depth. In some embodiments, the tissue depth indicia of thread 30 may include one or more ribs, spikes, bosses, or protrusions that interact with the surface of tissue to increase the insertion torque to achieve tactile indication.

Threaded portion 24 includes a distal thread 40 spaced apart from thread 30. Thread 40 extends between a proximal most end 42 and a distal most end 44. In some embodiments, end 44 includes a distal most end of tip 26. In some embodiments, end 44 does not include tip 26.

Thread 40 extends a distance along shaft 22 and includes a lead I2. In some embodiments, lead I2 includes an axial advance of a helix of thread 40 during one complete 360 degree rotation of thread 40. In some embodiments, lead I1 is equal to lead I2. In some embodiments, lead I1 is different than lead I2. In some embodiments, end 42 is disposed at a position located 10 mm from a distal most end of tip 26. In some embodiments, end 42 is disposed at a position located 10 mm from end 44, which does not include tip 26. Thread 40 extends distally from end 42 along shaft 22 to end 44 to facilitate tapping a desired depth for a bone fastener.

Thread 40 includes tissue depth indicia, such as, for example, an undercut 46 disposed adjacent end 42. Undercut 46 provides visual indicia of a depth of tissue penetration, such as for example, a depth d2, relative to vertebrae. In some embodiments, undercut 46 comprises a stopping point of thread 40 and/or tap 12 relative to vertebrae. In some embodiments depth d2 is substantially equal to 10 mm. In some embodiments, all or a portion of thread 40, for example, undercut 46 may be radiopaque. In some embodiments, thread 40 includes a plurality of undercuts 46, which may be spaced apart.

In some embodiments, undercut 46 is configured to generate a tactile feedback and indicate a stage of insertion and/or penetration of tap 12 along thread 40. In one embodiment, undercut 46 provides a tactile feel to a surgeon when tap 12 is inserted to a partial depth. In some embodiments, the tissue depth indicia of thread 40 may include one or more ribs, spikes, bosses, or protrusions that interact with the surface of tissue to increase the insertion torque to achieve tactile indication.

In some embodiments, undercut 46 is configured to generate a tactile feedback and indicate the proper stage of insertion. In one embodiment, undercut 46 provides a tactile feel to the surgeon when tap 12 is inserted to a partial depth. In some embodiments, thread 40 includes a plurality of undercuts 46. In some embodiments, the tissue depth indicia may include, such as, for example, one or more ribs, spikes, bosses, or protrusions that interact with the surface of tissue to increase the insertion torque to achieve the tactile indication.

In some embodiments, the tissue depth indicia is configured to be viewed by medical imaging, such as those described herein, and for example under fluoroscopy. In some embodiments, the tissue depth indicia may include markings that comprise a plurality of spaced apart graduations, as shown, for example, in FIG. 2. In some embodiments, the tissue depth indicia may include an analog, such as, for example, a dial with a numerical indicator of depth and/or digital display, such as, for example, LED and/or LCD. In some embodiments, the tissue depth indicia include human readable visual indicia, such as, for example, a label, color coding, alphanumeric characters or an icon. In some embodiments, the tissue depth indicia include human readable tactile indicia, such as, for example, raised portions, lowered portions or Braille. In some embodiments, the tissue depth indicia is a printed or written item in combination with a slot or groove, whereby the printed or written item is placed in the slot or groove to display information. In some embodiments, the tissue depth indicia may be applied as an adhesive label.

Thread 24 includes an intermediate portion 50 disposed between thread 30 and thread 40. Portion 50 includes a non-threaded surface 52. In some embodiments, surface 52 is an even surface. In some embodiments, surface 52 may have various surface configurations, such as, for example, arcuate, undulating, dimpled, polished and/or textured. Portion 50 extends between an end 54 and an end 56 along a distance d3. In some embodiments, distance d3 equals 4 mm. In some embodiments, distance d3 ranges between 0 through 10 mm. Undercut 36 is disposed adjacent end 54 of portion 50 and undercut 46 is disposed adjacent end 56 to facilitate determination of the position of thread 30, thread 40 and/or tap 12 relative to tissue, for example, vertebrae.

Figure 4:
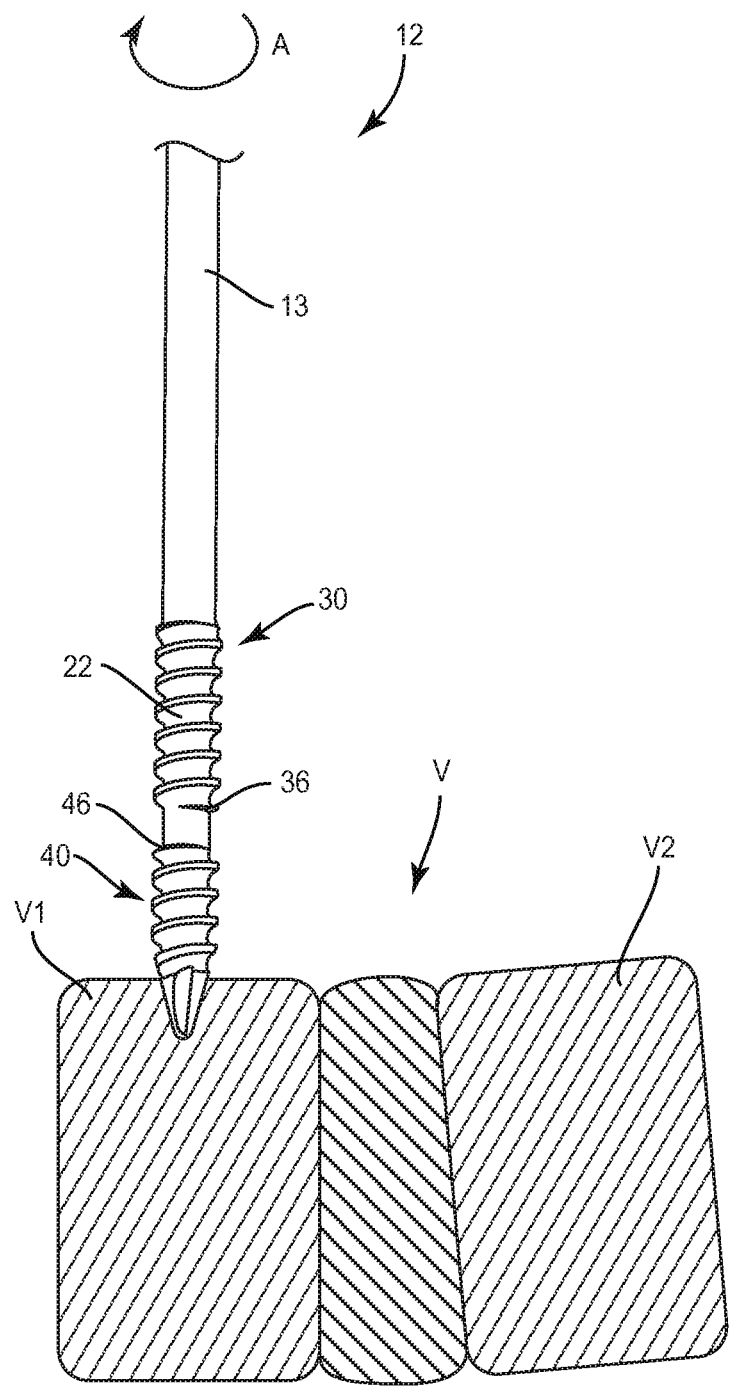
FIG. 4 is a side break away view of components of one embodiment of a surgical system in accordance with the principles of the present disclosure disposed with vertebrae.
Figure 5:
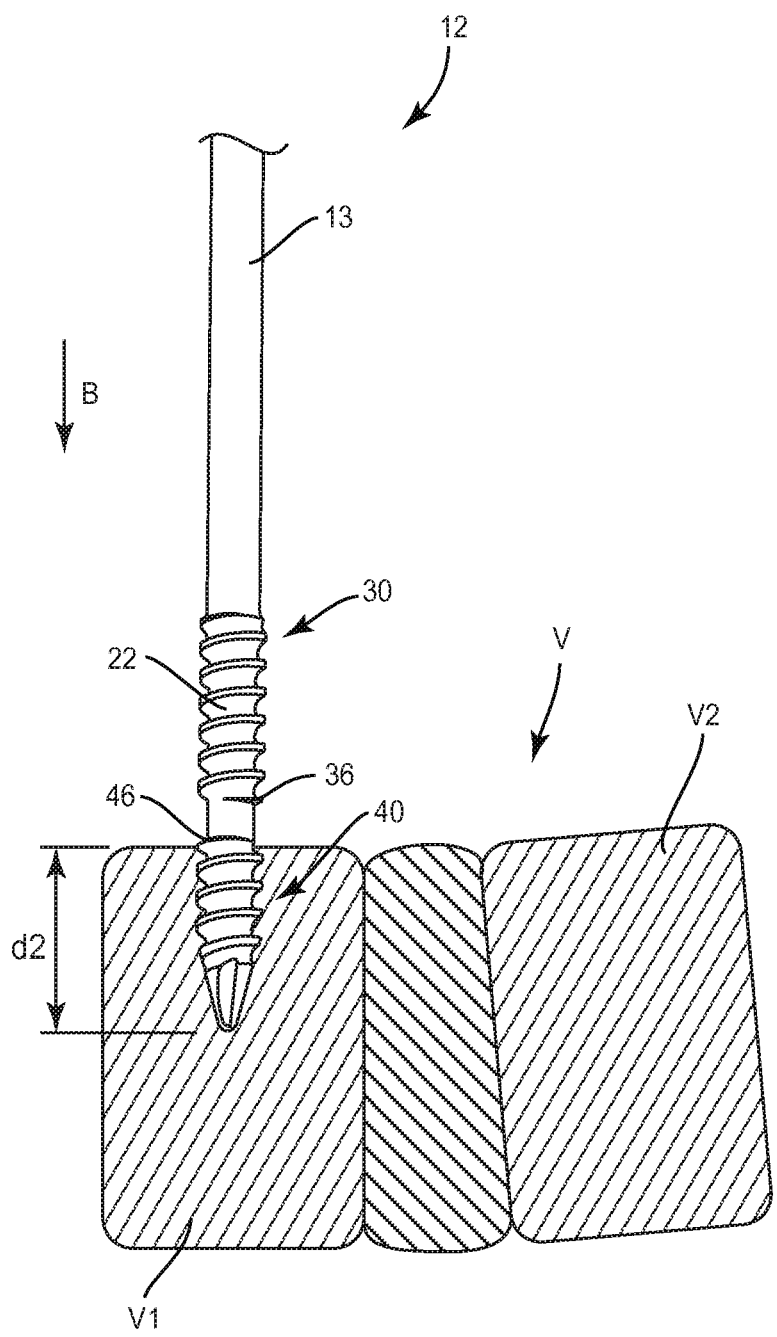
FIG. 5 is a side view of the components and vertebrae shown in FIG. 4.
Figure 6:
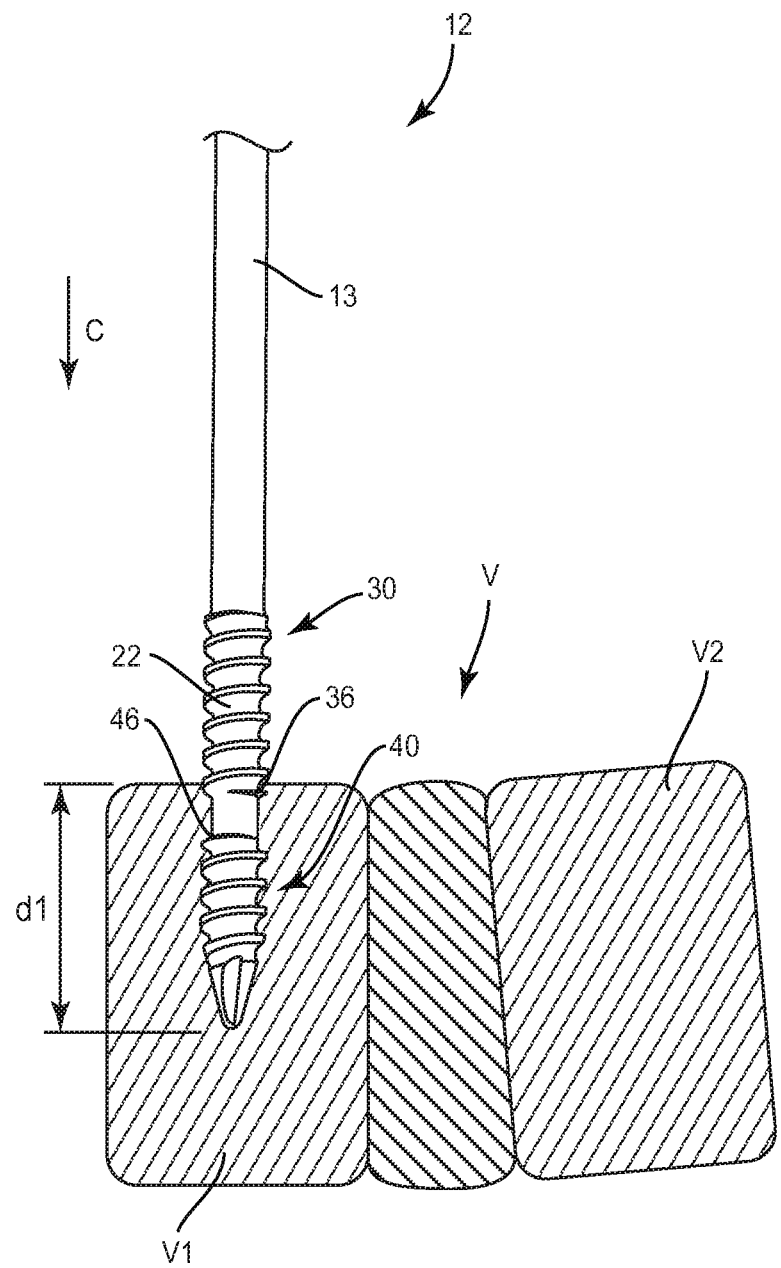
FIG. 6 is a side view of the components and vertebrae shown in FIG. 4.

In assembly, operation and use, surgical system 10, similar to the systems and methods described herein, is employed with a surgical procedure for treatment of a spinal disorder affecting a section of a spine of a patient, as discussed herein. For example, the components of surgical system 10 can be used with a surgical procedure for treatment of a condition or injury of an affected section of the spine including vertebrae V, as shown in FIGS. 4-6. In some embodiments, one or all of the components of surgical system 10 can be delivered or implanted as a pre-assembled device or can be assembled in situ. Surgical system 10 may be completely or partially revised, removed or replaced.

The components of surgical system 10 can be employed with a surgical treatment of an applicable condition or injury of an affected section of a spinal column and adjacent areas within a body, such as, for example, vertebrae V. In some embodiments, the components of surgical system 10 may be employed with one or a plurality of vertebra, such as, for example, vertebra V1 and vertebra V2. To treat a selected section of vertebrae V, a medical practitioner obtains access to a surgical site including vertebrae V in any appropriate manner, such as through incision and retraction of tissues. In some embodiments, the components of surgical system 10 can be used in any existing surgical method or technique including open surgery, mini-open surgery, minimally invasive surgery and percutaneous surgical implantation, whereby vertebrae V are accessed through a mini-incision, or sleeve that provides a protected passageway to the area. Once access to the surgical site is obtained, the particular surgical procedure can be performed for treating the spine disorder.

An incision is made in the body of a patient and a cutting instrument (not shown) creates a surgical pathway for delivery of components of surgical system 10 including tap 12, as described herein, adjacent an area within the patient's body, such as, for example, vertebra V1. In some embodiments, a dilator (not shown) is delivered through the surgical passageway adjacent a surgical site within the patient's body.

Tap 12 is positioned such that end 16 is disposed adjacent the surgical site at a substantially zero or contacting depth, as shown in FIG. 4. Tap 12 is rotated, in the direction shown by arrow A in FIG. 4, causing tap 12 to penetrate tissue to form a cavity therein to partially tap vertebra V1. As tap 12 is rotated, tap 12 translates axially into vertebra V1, in the direction shown by arrow B as shown in FIG. 5, to create a cavity for partial tapping of vertebra V1.

As tap 12 is translated, an external or male threaded portion of thread 40 engages vertebra V1 to form an internal or female thread in vertebra V1 and form the cavity therein for disposal and fixation with a bone fastener (not shown). Under fluoroscopy, tap 12 translates and undercut 46 provides visual indicia of depth of penetration d2, as described herein, of thread 40 and/or tap 12 in tissue relative to vertebra V1 to provide a visual reference or display of a partial tap of vertebra V1. In some embodiments, depth of penetration d2 equals 10 mm. In some embodiments, undercut 46 generates tactile feedback and indicates insertion and/or penetration of thread 40 in tissue of vertebra V1. In some embodiments, undercut 46 provides selective tactile feel to the surgeon of depth d2.

In some embodiments, tap 12 is further rotated such that tap 12 translates axially into vertebra V1, in the direction shown by arrow C in FIG. 6, to increase the depth of the cavity for disposal and fixation with the bone fastener. Under fluoroscopy, tap 12 translates and undercut 36 provides visual indicia of depth of penetration d1, as described herein, of thread 30 and/or tap 12 in tissue relative to vertebra V1 to provide a visual reference or display of a fully tapped cavity of vertebra V1 for disposal and fixation with the bone fastener. In some embodiments, depth of penetration d1 equals 14 mm. In some embodiments, undercut 36 generates tactile feedback and indicates insertion and/or penetration of thread 30 in tissue of vertebra V1. In some embodiments, undercut 36 provides selective tactile feel to the surgeon of depth d1.

In use, for treatment of a spinal disorder, a shaft of the bone fastener can be threaded and engaged with tissue of the cavity formed in vertebra V1 with tap 12. In some embodiments, the bone fastener is disposed adjacent vertebra V1 at a surgical site and is manipulated to drive, torque, insert or otherwise connect the bone fastener with vertebra V1. In some embodiments, surgical system 10 can be employed to create one or a plurality of cavities in one or more of vertebrae V.

Surgical system 10 can include one or a plurality of bone fasteners such as those described herein and/or fixation elements, which may be employed with a single vertebral level or a plurality of vertebral levels. In some embodiments, the one or more cavities formed in tissue with tap 12 and/or the bone fasteners disposed therewith may be engaged with vertebrae in various orientations, such as, for example, series, parallel, offset, staggered and/or alternate vertebral levels. In some embodiments, the bone fasteners and/or fixation elements may include one or a plurality of multi-axial screws, sagittal angulation screws, pedicle screws, mono-axial screws, uni-planar screws, fixed screws, tissue penetrating screws, conventional screws, expanding screws, wedges, anchors, buttons, clips, snaps, friction fittings, compressive fittings, expanding rivets, staples, nails, adhesives, posts, fixation plates and/or posts.

In some embodiments, surgical system 10 may comprise various instruments including the configuration of the present disclosure, such as, for example, inserters, extenders, reducers, spreaders, distractors, blades, retractors, clamps, forceps, elevators and drills, which may be alternately sized and dimensioned, and arranged as a kit.

In some embodiments, surgical system 10 includes an agent, which may be disposed, packed or layered within, on or about the components and/or surfaces of surgical system 10. In some embodiments, the agent may include bone growth promoting material, such as, for example, bone graft to enhance fixation with vertebrae V. The components of surgical system 10 can be made of radiolucent materials such as polymers. Radiomarkers may be included for identification under x-ray, fluoroscopy, CT or other imaging techniques. In some embodiments, the agent may include one or a plurality of therapeutic agents and/or pharmacological agents for release, including sustained release, to treat, for example, pain, inflammation and degeneration. Upon completion of the procedure, the surgical instruments, assemblies and non-implant components of surgical system 10 are removed from the surgical site and the incision is closed.

Figure 7:
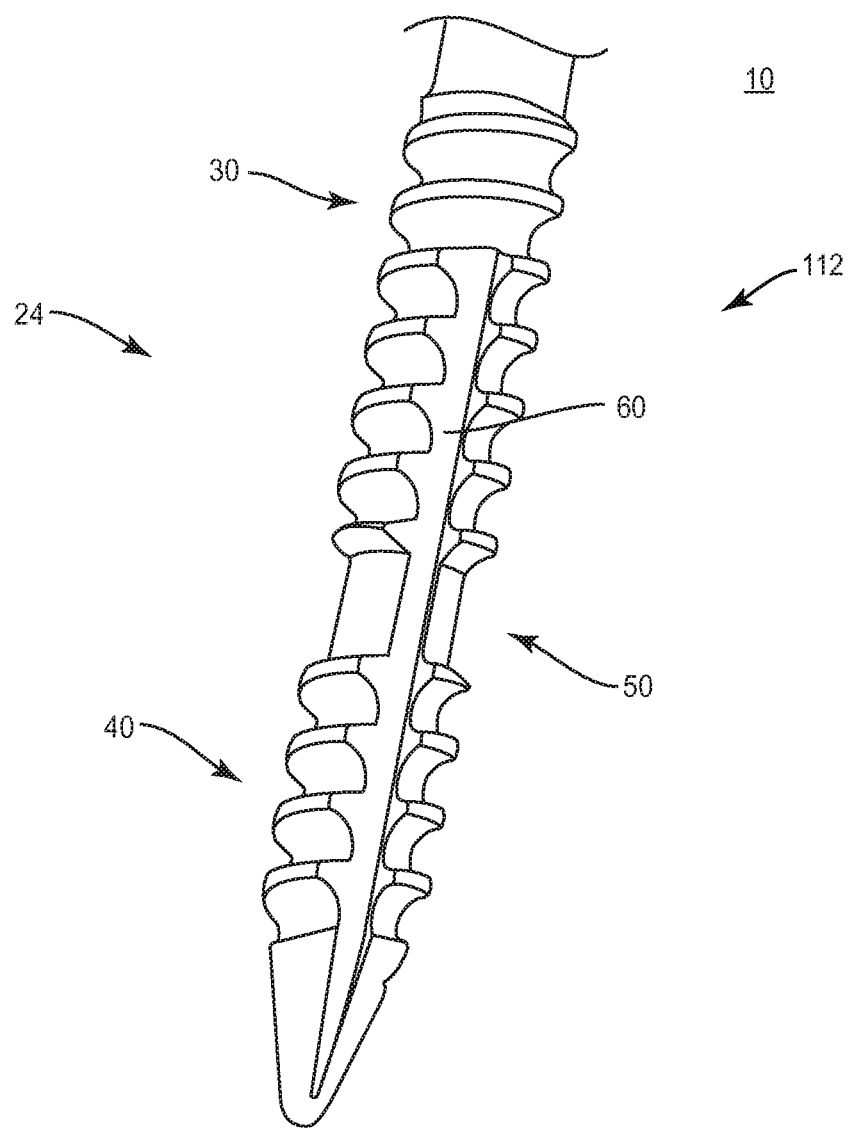
FIG. 7 is a perspective break away view of components of one embodiment of a surgical system in accordance with the principles of the present disclosure.

In one embodiment, as shown in FIG. 7, surgical system 10, similar to the systems and methods described with regard to FIGS. 1-6, comprises a tap 112, similar to tap 12, described herein, having threaded portion 24 including thread 30, thread 40 and portion 50. Tap 12 includes a longitudinal rib 60 axially disposed along threaded portion 24. Longitudinal rib 60 extends along thread 30, thread 40 and portion 50. Longitudinal rib 60 is configured to facilitate irrigation and/or removal of tissue at the surgical site.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A surgical instrument comprising:
a proximal end including a tool engagement surface; and
a distal end configured to form a threaded bore in vertebral tissue to receive an implant that is separate from the surgical instrument, the distal end including a first thread, a second thread spaced from the first thread and at least one tissue depth indicia, the first thread having a maximum length that is greater than a maximum length of the second thread, the distal end comprising a tapered tip, the second thread being positioned between the first thread and the tip, the first thread having a major diameter that is equal to a major diameter of the second thread, the first thread including a first lead and the second thread including a second lead, the leads being different.

2. A surgical instrument as recited in claim 1, wherein the first thread includes a first tissue depth indicia and the second thread includes a second tissue depth indicia.

3. A surgical instrument as recited in claim 1, wherein the first thread comprises a distal thread and the at least one tissue depth indicia includes a tissue depth indicator disposed adjacent a proximal most end of the distal thread.

4. A surgical instrument as recited in claim 1, wherein the first thread comprises a proximal thread and the at least one tissue depth indicia includes a tissue depth indicator disposed adjacent a distal most end of the proximal thread.

5. A surgical instrument as recited in claim 1, wherein the at least one tissue depth indicia includes an undercut of at least one of the threads.

6. A surgical instrument as recited in claim 1, wherein the at least one tissue depth indicia includes a plurality of undercuts of the threads.

7. A surgical instrument as recited in claim 1, further comprising an intermediate portion disposed between the ends.

8. A surgical instrument as recited in claim 7, wherein the intermediate portion comprises a non-threaded surface.

9. A surgical instrument as recited in claim 7, wherein the intermediate portion comprises an even surface.

10. A surgical instrument as recited in claim 7, wherein the at least one tissue depth indicia comprises a tissue depth indicator disposed adjacent a proximal most end of the intermediate portion and a tissue depth indicator disposed adjacent a distal most end of the intermediate portion.

11. A surgical instrument as recited in claim 1, wherein the at least one tissue depth indicia comprises a 10 mm tissue depth indicator and a 14 mm tissue depth indicator.

12. A surgical instrument as recited in claim 1, wherein the at least one tissue depth indicia comprises visual indicia.

13. A surgical instrument as recited in claim 1, wherein the at least one tissue depth indicia comprises tactile indicia.

14. A surgical instrument as recited in claim 1, wherein the tip is a self-tapping tip.

15. A surgical instrument as recited in claim 1, wherein the tip is a blunt tip.

16. A surgical instrument as recited in claim 1, wherein the tool engagement surface is connected to a powered actuator.

17. A surgical instrument comprising:
a proximal end including a tool engagement surface; and
a distal end configured to form a bore in vertebral tissue to receive an implant that is separate from the surgical instrument, the distal end including a proximal thread, a distal thread and an intermediate portion having an even surface disposed therebetween, the proximal thread having a maximum length that is greater than a maximum length of the distal thread, the distal end comprising a tapered tip, the distal thread being positioned between the proximal thread and the tip, the proximal thread having a major diameter that is equal to a major diameter of the distal thread, the proximal thread including a first lead and the distal thread including a second lead, the leads being different;
a first tissue depth indicator disposed adjacent a distal most end of the proximal thread; and
a second tissue depth indicator disposed adjacent a proximal most end of the distal thread.

18. A surgical system comprising:
a surgical instrument comprising a proximal end including an engagement surface, and a distal end configured to form a bore in vertebral tissue, the distal end including a first thread, a second thread spaced from the first thread and at least one tissue depth indicia, the first thread having a maximum length that is greater than a maximum length of the second thread, the distal end comprising a tapered tip, the second thread being positioned between the first thread and the tip, the first thread having a major diameter that is equal to a major diameter of the second thread, the first thread including a first lead and the second thread including a second lead, the leads being different;
an actuator connected with the engagement surface; and
a spinal implant configured for disposal with the bore.

* * * * *